(12) United States Patent
Hu et al.

(10) Patent No.: US 11,771,314 B2
(45) Date of Patent: Oct. 3, 2023

(54) INTRAORAL SCANNER

(71) Applicant: QISDA CORPORATION, Taoyuan (TW)

(72) Inventors: Sheng-Wen Hu, Taoyuan (TW); Ming-Kuen Lin, Taoyuan (TW)

(73) Assignee: Qisda Corporation, Taoyuan (TW)

( * ) Notice: Subject to any disclaimer, the term of this patent is extended or adjusted under 35 U.S.C. 154(b) by 151 days.

(21) Appl. No.: 17/322,918

(22) Filed: May 18, 2021

(65) Prior Publication Data
US 2021/0361154 A1 Nov. 25, 2021

(30) Foreign Application Priority Data
May 22, 2020 (TW) ................................ 109117040

(51) Int. Cl.
| | |
|---|---|
| *A61B 1/247* | (2006.01) |
| *G02B 7/04* | (2021.01) |
| *A61B 1/00* | (2006.01) |
| *A61B 1/06* | (2006.01) |
| *H04N 23/56* | (2023.01) |
| *H04N 23/50* | (2023.01) |

(52) U.S. Cl.
CPC .......... *A61B 1/247* (2013.01); *A61B 1/00009* (2013.01); *A61B 1/0605* (2022.02); *A61B 1/0655* (2022.02); *G02B 7/04* (2013.01); *H04N 23/56* (2023.01); *H04N 23/555* (2023.01)

(58) Field of Classification Search
CPC ... A61B 1/247; A61B 1/00009; A61B 1/0605; A61B 1/0655; A61B 1/00006; A61B 1/00096; A61B 1/00188; A61B 1/042; A61B 1/0669; G02B 7/04; G02B 26/0816; H04N 5/2256; H04N 2005/2255
See application file for complete search history.

(56) References Cited

U.S. PATENT DOCUMENTS

| | | | |
|---|---|---|---|
| 2005/0267335 A1* | 12/2005 | Okada ................ | A61B 1/00183 600/173 |
| 2007/0216781 A1* | 9/2007 | Miyanohara ....... | H04N 21/4223 348/E5.065 |
| 2017/0272632 A1* | 9/2017 | Wan ...................... | G01S 7/4817 |
| 2020/0170497 A1* | 6/2020 | Chang .................... | H04N 23/55 |
| 2021/0045637 A1* | 2/2021 | Chang .................... | A61C 19/04 |
| 2021/0177555 A1* | 6/2021 | Chang ................... | H04N 13/254 |

FOREIGN PATENT DOCUMENTS

| | | |
|---|---|---|
| CN | 109124576 A | 1/2019 |
| JP | 2010-246580 A | 11/2010 |

* cited by examiner

*Primary Examiner* — Richard A Hansell, Jr.

(57) ABSTRACT

An intraoral scanner includes a projecting module, an image-capturing module, a linkage structure, and a manipulation part. The projecting module includes a first lens device and a light source. Light emitted by the light source is projected out of the intraoral scanner by the first lens device. The image-capturing module includes a second lens device and an image sensor. The image sensor receives the light from the outside of the intraoral scanner through the second lens device. The manipulation part is exposed from the intraoral scanner and is mechanically linked with the first or second lens device through the linkage structure. Therein, the manipulation part is operable to correspondingly move at least one first lens of the first lens device or at least one second lens of the second lens device through the linkage structure, so as to adjust a scanning zone of the intraoral scanner.

11 Claims, 6 Drawing Sheets

INTRAORAL SCANNER

BACKGROUND OF THE INVENTION

1. Field of the Invention

The present invention relates to an intraoral scanner.

2. Description of the Prior Art

Current intraoral scanners usually use a probe to extend into the oral cavity to scan the oral cavity. In principle, the intraoral scanner will project markings onto the surface of the oral cavity, capture an image of the surface of the oral cavity that contains the markings, and then analyze the image to form a 3D scan result. No matter during projecting light or capturing light, lens will be used. Therefore, in principle, the intraoral scanner can only scan its scanning zone (or spatial range). However, in the actual use of the intraoral scanner, sufficient space required for operating the intraoral scanner may not be obtained because of the patient's current situation (for example, the patient is in pain and cannot open his mouth properly, the operation space required to scan different portions of the oral cavity is different, the difference between the oral structures of adults and children, etc.), so that the surface to be scanned does not fall completely within the scanning zone and cannot be scanned effectively. Therefore, the current internal scanner adopts a fixed scanning zone design, which is still limited and inconvenient in use.

SUMMARY OF THE INVENTION

An objective of the invention is to provide an intraoral scanner. The intraoral scanner provides users an adjustable scanning zone, which increases the use flexibility of the internal scanner so as to adapt to more usage scenarios.

An intraoral scanner according to the invention includes a projecting module, an image-capturing module, a linkage structure, and a manipulation part. The projecting module includes a first lens device and a light source. Light emitted by the light source is projected out of the intraoral scanner through the first lens device. The image-capturing module includes a second lens device and an image sensor. The image sensor receives the light from outside of the intraoral scanner through second lens device. The manipulation part is exposed form the intraoral scanner and mechanically linked with the first lens device or the second lens device through the linkage structure. Therein, the manipulation part is operable to correspondingly move at least one first lens of the first lens device or at least one second lens of the second lens device through the linkage structure, so as to adjust a scanning zone of the intraoral scanner. Thereby, the user can manipulate the manipulation part to adjust the distance of the scanning zone relative to the intraoral scanner, which increases the use flexibility of the intraoral scanner and therefore can solve the problems in the prior art that the usage of the intraoral scanners adopting the fixed scanning zone design is limited and inconvenient or reduce the degree of the limitation and inconvenience.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
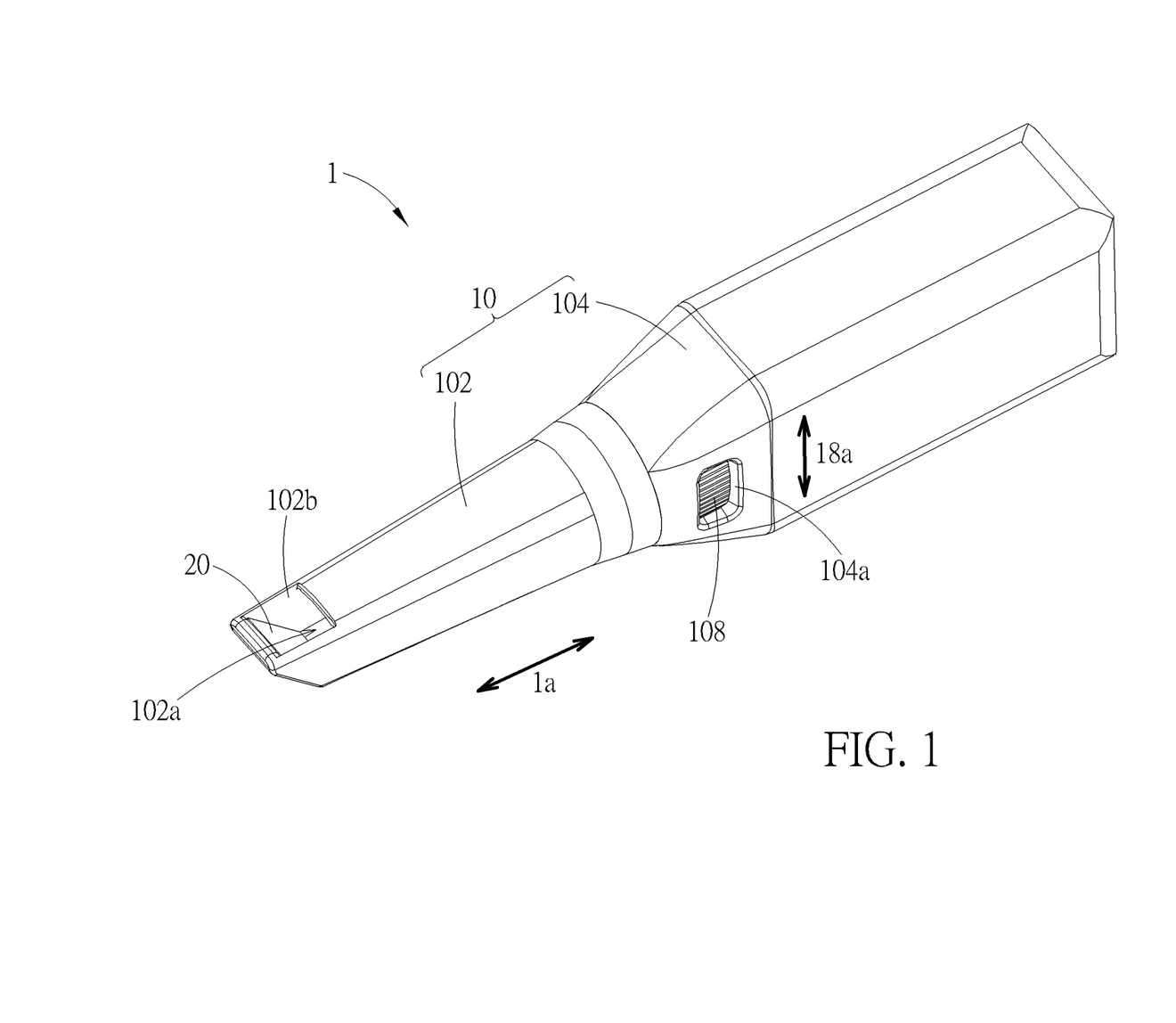
FIG. 1 is a schematic diagram illustrating an intraoral scanner according to an embodiment.
Figure 2:
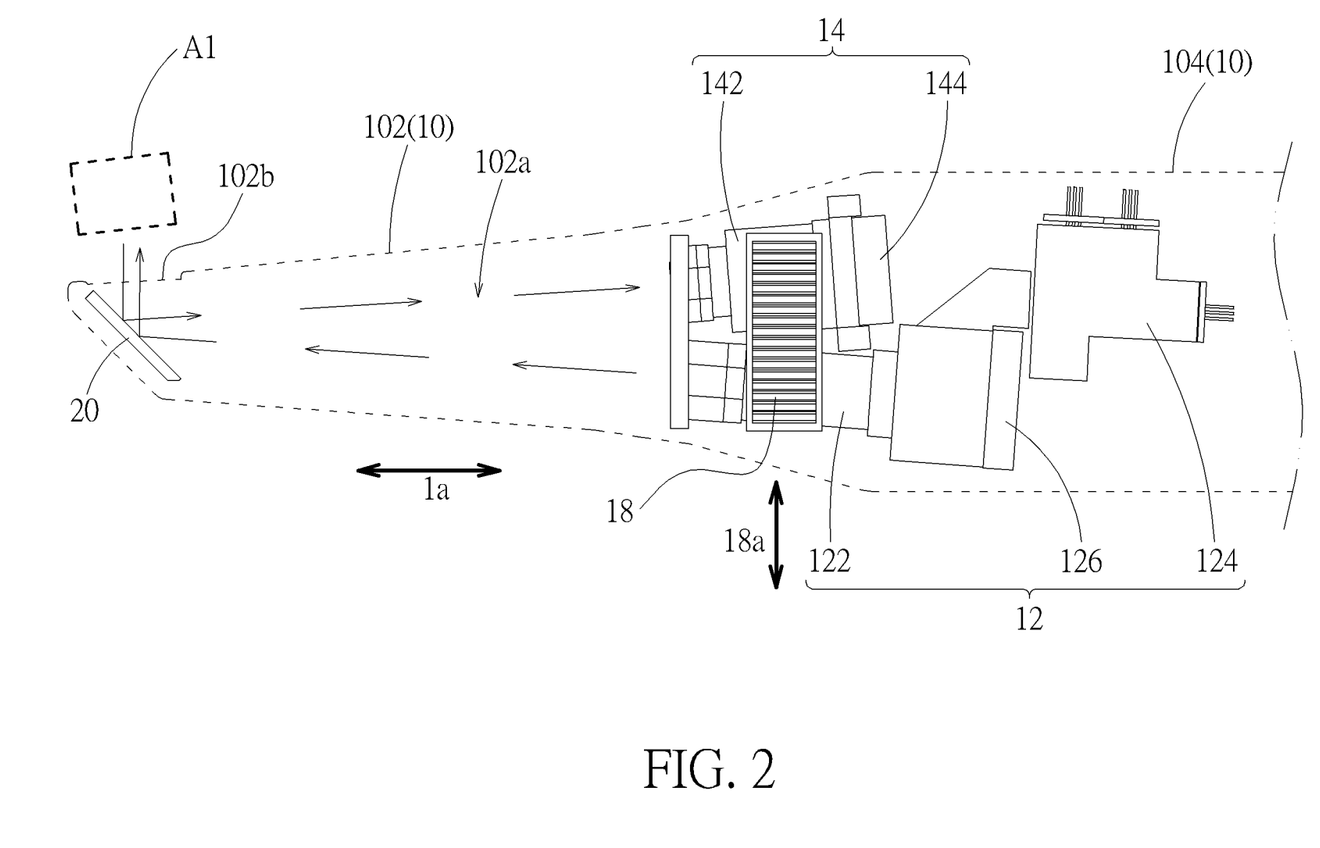
FIG. 2 is a side view of the intraoral scanner in FIG. 1; therein, the profile of a device housing is shown in dashed lines.
Figure 3:
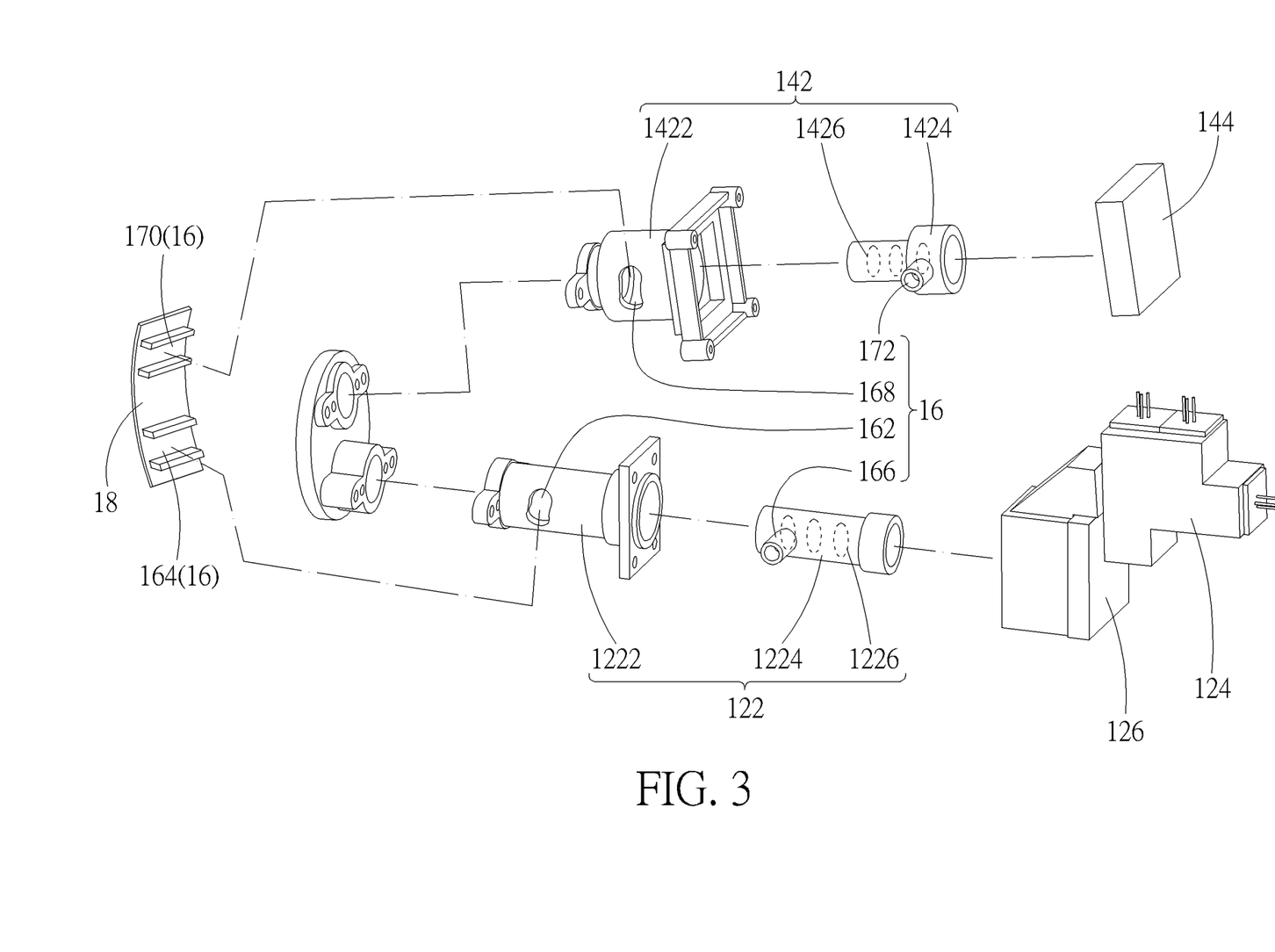
FIG. 3 is an exploded view of a projecting module, an image-capturing module, a linkage structure, and a manipulation part of the intraoral scanner in FIG. 2.

Please refer to FIG. 1 to FIG. 3. An intraoral scanner 1 according to an embodiment includes a device housing 10, a projecting module 12, an image-capturing module 14, a linkage structure 16, a manipulation part 18, and a light reflector 20. The projecting module 12, the image-capturing module 14, the linkage structure 16, and the light reflector 20 are accommodated in the device housing 10. The manipulation part 18 is connected to the linkage structure 16 and exposed from the device housing 10 (or the intraoral scanner 1). In practice, the device housing 10 also accommodates other needed components, e.g. a controller (e.g. electrically connected to the projecting module 12 and the image-capturing module 14 for controlling the operation thereof), a power source, a heater, and so on. The projecting module 12 includes a first lens device 122 and a light source 124. The image-capturing module 14 includes a second lens device 142 and an image sensor 144. Light (of which the path is indicated by arrows in the figures) emitted by the light source 124 is projected out of the device housing 10 (or the intraoral scanner 1) through the first lens device 122 and the light reflector 20. The image sensor 144 receives the light from outside the device housing 10 (or the intraoral scanner 1) and environmental light through the light reflector 20 and the second lens device. The manipulation part 18 is mechanically linked with the first lens device 122 and the second lens device 142 through the linkage structure 16, so as to adjust a scanning zone A1 (indicated by a dashed rectangle in FIG. 2) of the intraoral scanner 1. Object surfaces (e.g. surfaces of teeth and gum, including image such as marking lines projected by the projecting module 12 thereon) within the scanning zone A1 can be effectively captured by the image sensor 144 (e.g. the captured image is clear or acceptable resolution).

Furthermore, in the embodiment, in the projecting module 12, the light emitted by the light source 124 is modulated by a digital micromirror device 126 to be projected out of the intraoral scanner 1 through the first lens device 122. The image sensor 144 can be realized by a complementary metal oxide semiconductor sensor; however, it is not limited thereto in practice. For drawing simplification, the digital micromirror device 126 and the image sensor 144 are shown by a rectangle block respectively in the figures.

Figure 4:
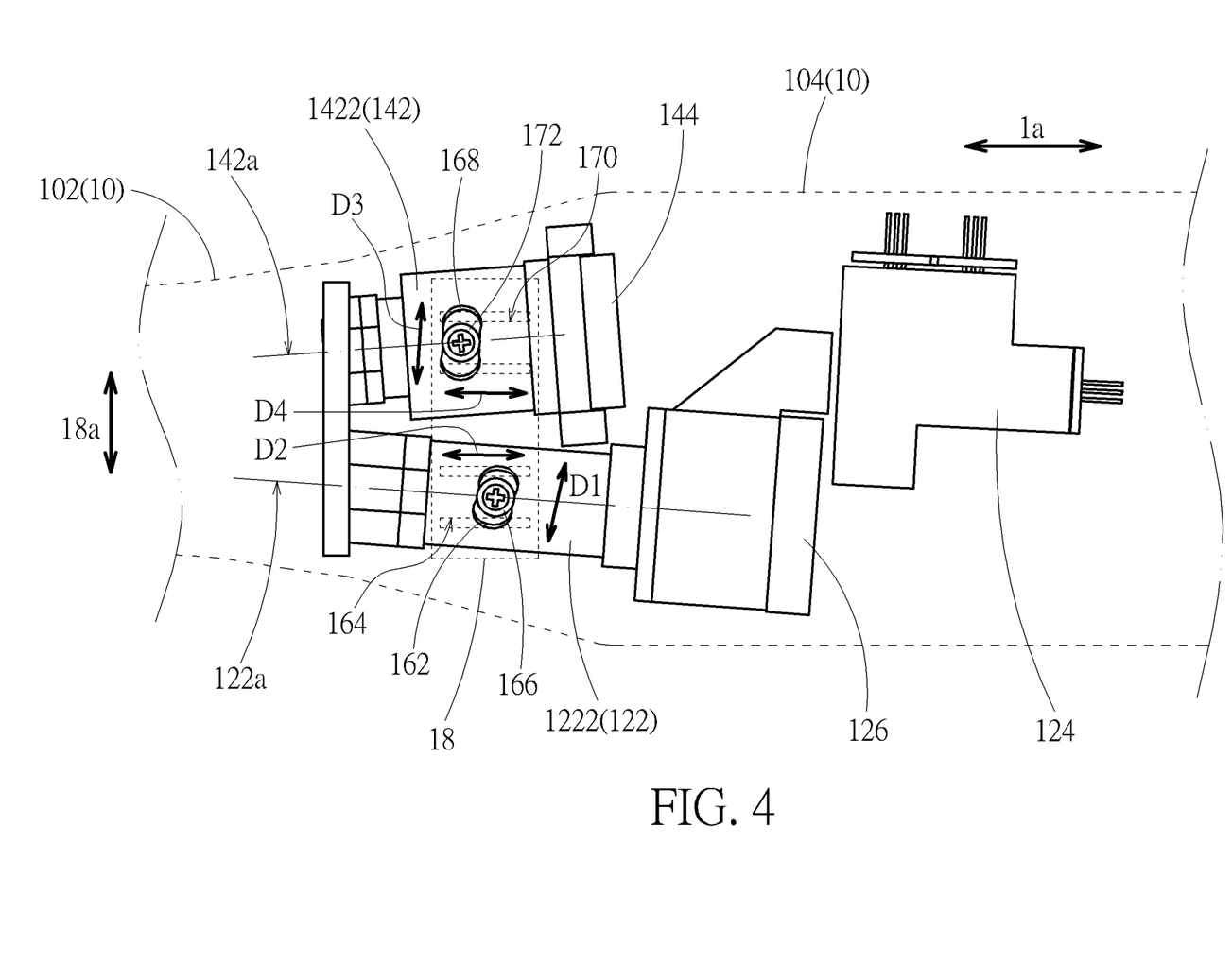
FIG. 4 is a schematic diagram illustrating the mechanical linkage of the manipulation part with the projecting module and the image-capturing module through the linkage structure in FIG. 2; therein, the profiles of the manipulation part and the device housing are shown in dashed lines.

Please also refer to FIG. 4. In the embodiment, the first lens device 122 includes a casing 1222, a lens bracket 1224 slidably disposed in the casing 1222, and a plurality of first lenses 1226 (of which the profiles in the lens bracket 1224 are shown by dashed circles) disposed on the lens bracket 1224. The first lenses 1226 are slidably disposed in the casing 1222 through the lens bracket 1224. The linkage structure 16 includes a first guiding slot 162, a second guiding slot 164, and a guiding post 166. The first guiding slot 162 is disposed on the casing 1222 (e.g. but not limited to being structurally integrated with the casing 1222 to be a single part) and extends in a first direction D1 (indicated by a double-headed arrow in FIG. 4). The second guiding slot 164 is disposed on the manipulation part 18 (e.g. but not limited to being structurally integrated with the manipulation part 18 to be a single part) and extends in a second direction D2 (indicated by a double-headed arrow in FIG. 4). The guiding post 166 is slidably disposed in the first guiding slot 162 and the second guiding slot 164. The guiding post 166 is connected to the first lenses 1226 through the lens bracket 1224 (i.e. connected to the lens bracket 1224, e.g. but not limited to being structurally integrated with the lens bracket 1224 to be a single part or being fixed on the lens bracket 1224 with screw), so that the guiding post 166 can move the first lenses 1226. The first lens device 122 has an optical axis 122a (indicated by a chain line in FIG. 4). The first direction D1 and the optical axis 122a are not perpendicular to each other. The manipulation part 18 is movable along a manipulation direction 18a (indicated by a double-headed arrow in FIG. 1 and FIG. 4). The first direction D1, the second direction D2, and the manipulation direction 18a are not parallel to each other. Thereby, a movement of the manipulation part 18 along the manipulation direction 18a (e.g. by a user moving the manipulation part 18) will cause a movement of the first lenses 1226 along the optical axis 122a.

In practice, based on the angle setting relationship between the first direction D1, the second direction D2, the manipulation direction 18a, and the optical axis 122a, there is a proportional relationship between the magnitudes of the two movements mentioned above. Therefore, it is possible to obtain the required proportional relationship by designing the angle setting relationship, for example, for improving the accuracy of adjusting the scanning zone A1 by the user through the adjustment part 18. In the embodiment, the first direction D1 and the optical axis 122a form an acute angle larger than 45 degrees. The second direction D2 is perpendicular to the manipulation direction 18a. However, it is not limited thereto in practice. Furthermore, in the embodiment, the intraoral scanner 1 is a handheld intraoral scanner having a substantially elongated structure. The intraoral scanner 1 (or the device housing 10 thereof) has a longitudinal direction 1a (indicated by a double-headed arrow in FIG. 1, FIG. 2, and FIG. 4) perpendicular to the manipulation direction 18a. This structural configuration is convenient for the user to manipulate the manipulation part 18 (e.g. by using a thumb while holding the intraoral scanner 1).

In the embodiment, the second lens device 142 includes a casing 1422, a lens bracket 1424 slidably disposed in the casing 1422, and a plurality of second lenses 1426 (of which the profiles in the lens bracket 1424 are shown by dashed circles) disposed on the lens bracket 1424. The second lenses 1426 are slidably disposed in the casing 1422 through the lens bracket 1424. In the embodiment, the linkage structure 16 is connected to the first lens device 122 and the second lens device 142 by similar connection structures; however, it is not limited thereto in practice. Therein, the linkage structure 16 includes another first guiding slot 168, another second guiding slot 170, and another guiding post 172. The first guiding slot 168 is disposed on the casing 1422 (e.g. but not limited to being structurally integrated with the casing 1422 to be a single part) and extends in a first direction D3 (indicated by a double-headed arrow in FIG. 4). The second guiding slot 170 is disposed on the manipulation part 18 (e.g. but not limited to being structurally integrated with the manipulation part 18 to be a single part) and extends in a second direction D4 (indicated by a double-headed arrow in FIG. 4). The guiding post 172 is slidably disposed in the first guiding slot 168 and the second guiding slot 170. The guiding post 172 is connected to the second lenses 1426 through the lens bracket 1424 (i.e. connected to the lens bracket 1424, e.g. but not limited to being structurally integrated with the lens bracket 1424 to be a single part), so that the guiding post 172 can move the second lenses 1426. The second lens device 142 has an optical axis 142a (indicated by a chain line in FIG. 4). The first direction D3 and the optical axis 142a are not perpendicular to each other. The first direction D3, the second direction D4, and the manipulation direction 18a are not parallel to each other. Thereby, a movement of the manipulation part 18 along the manipulation direction 18a (e.g. by the user moving the manipulation part 18) will cause a movement of the second lenses 1426 along the optical axis 142a. Furthermore, in the embodiment, the optical axis 122a of the first lens device 122 and the optical axis 142a of the second lens device 142 are not parallel to each other. For descriptions about the angle setting of the first direction D3, the second direction D4, and the optical axis 142a relative to the manipulation direction 18a, please refer to the relevant descriptions of the connection of the first lens device 122 with the linkage structure 16, which will not be described in addition.

Therefore, in the embodiment, the user can change the projection and imaging optical conditions (including but not limited to image distance, object distance, focal length, and so on) of the projecting module 12 and the image-capturing module 14 by moving the manipulation part 18, so as to adjust the position and size of the scanning zone A1 relative to the intraoral scanner 1 (or the device housing 10 thereof). In practice, the linkage structure 16 can be designed to be connected only to the first lens device 122 (of the projecting module 12) or the second lens device 142 (of the image-capturing module 14). This structural configuration also can allow the user to move the manipulation part 18 to adjust the scanning zone A1. Furthermore, in practice, two ends of the first guiding slot 162 or the first guiding slot 168 can be set as positioning points for adjusting the scanning zone A1. For example, when the guiding posts 166 and 172 are moved to one end of the first guiding slots 162 and 168 respectively by the manipulation part 18, the scanning zone A1 is relatively close to the intraoral scanner 1; when the guiding posts 166 and 172 are moved to the other end of the first guiding slots 162 and 168 respectively by the manipulation part 18, the scanning zone A1 is relatively far away from the intraoral scanner 1. This design helps the user to identify the positioning points of the scanning zone A1, which is convenient for the user to adjust. Furthermore, it is practicable to form more indication marks on the device housing 10 for the user to align when moving the manipulation part 18. Each indication mark can correspond to one positioning point of the scanning zone A1. In addition, in the embodiment, the first guiding slot 162 has a slightly 8-shaped profile in the first direction D1. The profile has two wide end portions and a narrow middle portion, which help to position the guiding post 166 at the two ends. The above also can be applied to the first guiding slot 168 and will not be repeated.

Figure 5:
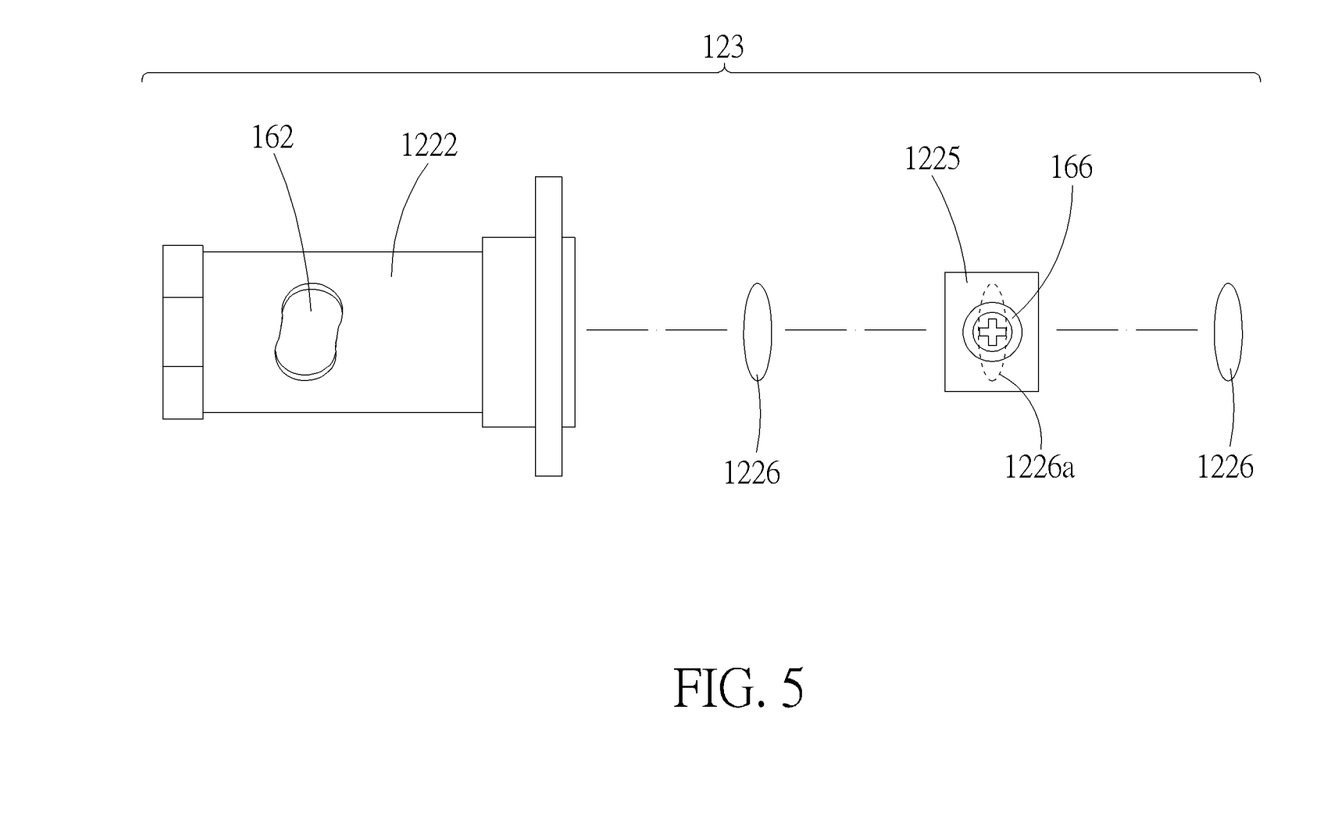
FIG. 5 is an exploded view of a first lens device according to another embodiment.
Figure 6:
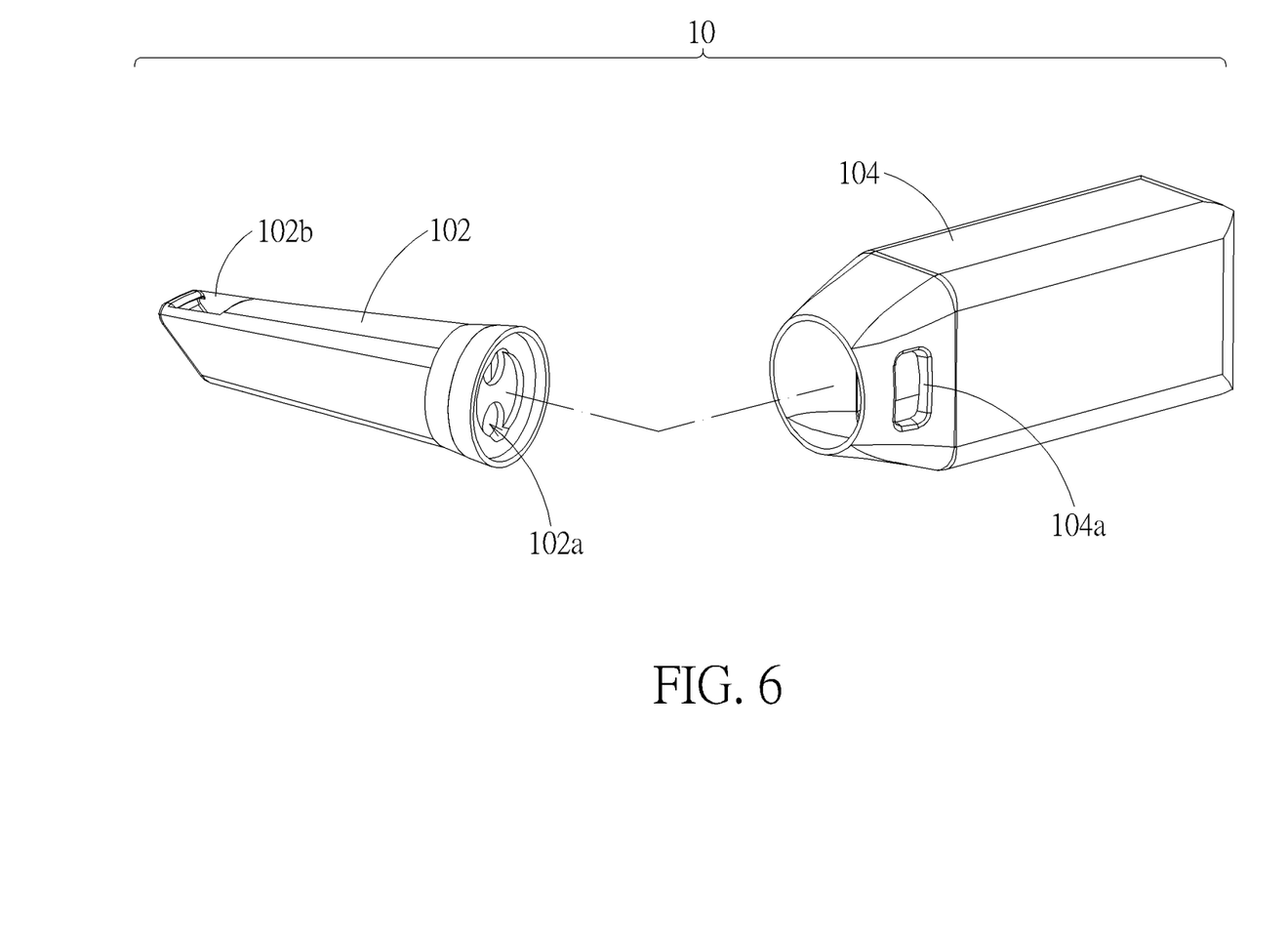
FIG. 6 is an exploded view of the device housing of the intraoral scanner in FIG. 1.

As described above, in the embodiment, for the first lens device 122, the manipulation part 18 can moves the first lenses 1226 at the same time through the linkage structure 16; however, it is not limited thereto in practice. For example, in a first lens device 123 shown in FIG. 5 according to an embodiment, a lens bracket 1225 thereof carries one first lens 1226*a* (of which the profile in the lens bracket 1225 is shown by a dashed circle) of the first lenses 1226; the rest of the first lenses 1226 is fixed to the casing 1222. Thereby, the first lens 1226*a* can be driven to move relative to the other first lenses 1226 by the manipulation part 18 (e.g. by the user moving the manipulation part 18), which also can change the projection optical conditions (including but not limited to image distance, object distance, focal length, and so on) of the projecting module 12, so as to adjust the scanning zone of the intraoral scanner (similar to the scanning zone A1 in FIG. 2). Similarly, the foregoing description about the variation of the first lens device 122 (i.e. the first lens device 123) also can be applied to the second lens device 142, which will not be described in addition.

Please refer to FIG. 1 to FIG. 3 and FIG. 6. In the embodiment, the device housing 10 includes a front housing 102 and a rear housing 104 connected to the front housing 102. The projecting module 12, the image-capturing module 14, and the linkage structure 16 are disposed in the rear housing 104. The light reflector 20 is disposed in the front housing 102. The front housing 102 has a cavity 102*a* and an opening 102*b* communicating with the cavity 102*a*. The light reflector 20 is fixedly disposed in the cavity 102*a* toward the opening 102*b*. The opening 102*b* faces the scanning zone A1. Therefore, the light emitted by the light source 124 passes through the first lens device 122 and then is reflected by the light reflector 20 to be projected out through the opening 120*b*. The image sensor 144 through the second lens device 142 receives the light that enter the cavity 102*a* through the opening 102 from outside the intraoral scanner 1 (or the device housing 10 thereof) so as to be reflected by the light reflector 20. The opening 102*b* is located at an end portion of the device housing 10 in the longitudinal direction 1*a*, which helps the intraoral scanner 1 to extend into the oral cavity more (e.g. to capture more complete images of surfaces of teeth and gum).

Furthermore, in the embodiment, the rear housing 104 has a window 104*a*. The manipulation part 18 is exposed from the window 102. The manipulation direction 18*a* is perpendicular to the longitudinal direction 1*a*, which facilitates the manipulation of the user (e.g. the user uses his thumb to toggle up and down in the view point of FIG. 2); however, it is not limited thereto. For example, the manipulation direction 18*a* and the longitudinal direction 1*a* can be disposed in another acute angle (e.g. parallel or not parallel), in which the user can easily manipulate the manipulation part 18 by his thumb. In addition, in the embodiment, the manipulation part 18 does not directly contact the device housing 10. However, it is practicable to design the manipulation part 18 and the device housing 10 to be slidably engaged with each other. For example, two sliding slots are formed on the inner side of the device housing 10 and extend along the manipulation direction 18*a*. Two side edges of the manipulation part 18 are slidably engaged with the two sliding slots respectively. For another example, the manipulation part 18 has two step structures extending along the manipulation direction 18*a* at its two sides respectively. The manipulation part 18 is slidably engaged with the window 104*a* through the step structures. This structural configuration is conducive to improving the stability of the sliding movement of the manipulation part 18 along the manipulation direction 18*a*.

Furthermore, in practice, an appropriate structural design can be used to make the manipulation part 18 substantially ring-shaped (extending perpendicular to the vertical manipulation direction 18*a*), which is sleeved on the device housing 10 and can also be used as an appearance decoration ring of the device housing 10 at the same time. The ring-shaped structure protrudes inwards to from a connecting portion (e.g. on which the second guiding slots 164 and 170 are formed), which extends into the device housing 10 through the window 104*a* to be slidably engaged with the guiding posts 166 and 172. Therein, the window 104*a* can structurally constrain the movement of the connecting portion along the manipulation direction 18*a*. In this instance, two ends of the window 104*a* along the manipulation direction 18*a* can also be used as positioning points for adjusting the scanning zone A1. For example, when the manipulation part 18 is moved to be stopped at one end by the window 104*a*, the scanning zone A1 is relatively close to the intraoral scanner 1; when the manipulation part 18 is moved to be stopped at the other end by the window 104*a*, the scanning zone A1 is relatively far away from the intraoral scanner 1. Furthermore, in practice, edges of the window 104*a* can form a plurality of positioning positions (e.g. realized by a wavy elastic structure). The ring-shaped structure can be moved along the manipulation direction 18*a* so that the connecting portion can be selectively held at one of the positioning positions. Furthermore, in practice, the edges of window 104*a* and the connecting portion can be connected in a transition fit so as to provide continuous adjustment of the scanning zone A1.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An intraoral scanner, comprising:
a projecting module, comprising a first lens device and a light source, light emitted by the light source being projected out of the intraoral scanner through the first lens device;
an image-capturing module, comprising a second lens device and an image sensor, the image sensor receiving the light from outside of the intraoral scanner through the second lens device;
a linkage structure; and
a manipulation part, exposed from the intraoral scanner and mechanically linked with the first lens device or the second lens device through the linkage structure;
wherein the manipulation part is operable to correspondingly move at least one first lens of the first lens device or at least one second lens of the second lens device through the linkage structure, so as to adjust a scanning zone of the intraoral scanner;
wherein the first lens device or the second lens device that is mechanically linked with the manipulation part has a casing, the at least one first lens or the at least one second lens is correspondingly slidably disposed in the casing, the linkage structure comprises a first guiding slot, a second guiding slot, and a guiding post, the first guiding slot is disposed on the casing and extends in a first direction, the second guiding slot is disposed on the manipulation part and extends in a second direction, the guiding post is connected to the at least one first lens or the at least one second lens and is slidably disposed in the first guiding slot and the second guiding slot, the first lens device or the second lens device that is mechanically linked with the manipulation part has an optical axis, the first direction is not perpendicular to the optical axis, the manipulation part is movable along a manipulation direction, and the first direction, the second direction, and the manipulation direction are not parallel to each other.

2. The intraoral scanner according to claim 1, wherein the first direction and the optical axis form an acute angle, larger than 45 degrees.

3. The intraoral scanner according to claim 1, wherein the second direction is perpendicular to the manipulation direction.

4. The intraoral scanner according to claim 1, having a longitudinal direction, perpendicular to the manipulation direction.

5. The intraoral scanner according to claim 1, wherein the at least one first lens or the at least one second lens that is connected to the guiding post is multiple in number, the guiding post is correspondingly connected to one of the at least one first lens or the at least one second lens, and the first lens or the second lens that is connected to the guiding post is driven to move relative to the rest of the at least one first lens or the at least one second lens by the manipulation part.

6. The intraoral scanner according to claim 1, wherein the at least one first lens is multiple in number, the manipulation part is connected to one of the at least one first lens through the linkage structure, and the first lens connected to the manipulation part is driven to move relative to the rest of the at least one first lens by the manipulation part.

7. The intraoral scanner according to claim 1, wherein the manipulation part is mechanically linked with the first lens device and the second lens device at the same time through the linkage structure, and the manipulation part is operable to move the at least one first lens of the first lens device and the at least one second lens of the second lens device at the same time, so as to adjust the scanning zone of the intraoral scanner.

8. The intraoral scanner according to claim 7, wherein the first lens device has a first optical axis, the second lens device has a second optical axis, and the first optical axis and the second optical axis are not parallel to each other.

9. The intraoral scanner according to claim 1, further comprising a device housing, wherein the device housing has a window and accommodates the projecting module and the image-capturing module, and the manipulation part is slidably disposed on the device housing and exposed from the window.

10. The intraoral scanner according to claim 9, wherein the device housing has a longitudinal direction, and the manipulation direction is perpendicular to the longitudinal direction.

11. The intraoral scanner according to claim 1, further comprising a device housing and a light reflector, wherein the device housing accommodates the projecting module and the image-capturing module and has a cavity, an opening communicated with the cavity, and a longitudinal direction, the opening is located at an end portion of the device housing along the longitudinal direction and faces the scanning zone, the manipulation part is exposed from the device housing, the manipulation direction and the longitudinal direction are not parallel to each other, the light reflector faces the opening and is fixedly disposed in the cavity, the light emitted by the light source passes through the first lens device and is reflected by the light reflector to be projected out through the opening, the image sensor through the second lens device receives the light that enters the cavity through the opening from outside the intraoral scanner so as to be reflected by the light reflector.

* * * * *